United States Patent
Olivares Antunez et al.

(10) Patent No.: US 12,174,169 B2
(45) Date of Patent: Dec. 24, 2024

(54) APPARATUS AND METHOD FOR MEASURING SETTLING OF WEIGHTING MATERIALS IN DRILLING AND COMPLETION FLUIDS

(71) Applicant: SAUDI ARABIAN OIL COMPANY, Dhahran (SA)

(72) Inventors: Tulio D. Olivares Antunez, Khobar (SA); Abdullah A. Abahussain, Dhahran (SA); Rafael M. Pino, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 239 days.

(21) Appl. No.: 17/576,182

(22) Filed: Jan. 14, 2022

(65) Prior Publication Data
US 2023/0228729 A1    Jul. 20, 2023

(51) Int. Cl.
| | |
|---|---|
| *G01N 33/28* | (2006.01) |
| *C09K 8/14* | (2006.01) |
| *C09K 8/34* | (2006.01) |
| *G01N 9/04* | (2006.01) |
| *G01N 9/36* | (2006.01) |
| *E21B 49/08* | (2006.01) |

(52) U.S. Cl.
CPC ........... *G01N 33/2823* (2013.01); *C09K 8/14* (2013.01); *C09K 8/34* (2013.01); *G01N 9/04* (2013.01); *G01N 9/36* (2013.01); *E21B 49/08* (2013.01); *E21B 2200/20* (2020.05)

(58) Field of Classification Search
CPC ........ G01N 9/04; G01N 9/36; G01N 33/2823; C09K 8/14; C09K 8/34
See application file for complete search history.

(56) References Cited

U.S. PATENT DOCUMENTS

| | | |
|---|---|---|
| 6,330,826 B1 | 12/2001 | Meeten |
| 6,584,833 B1 | 7/2003 | Jamison et al. |
| 7,398,159 B2 | 7/2008 | Venkataramanan et al. |
| 8,393,207 B2 | 3/2013 | Fujisawa et al. |
| 9,187,966 B2 | 11/2015 | Kulkarni et al. |
| 9,194,972 B2 | 11/2015 | Van Der Zwaag et al. |
| 10,030,498 B2 * | 7/2018 | Kupferschmid ......... G01N 9/24 |

(Continued)

FOREIGN PATENT DOCUMENTS

| | | |
|---|---|---|
| CN | 106646277 A | 5/2017 |
| CN | 111441397 A | 7/2020 |

OTHER PUBLICATIONS

Elkatatny "Enhancing the Stability of Invert Emulsion Drilling Fluid for Drilling in High-Pressure High-Temperature Conditions," Energies 2018, 2393 (Year: 2018).*

(Continued)

*Primary Examiner* — John Fitzgerald
(74) *Attorney, Agent, or Firm* — Osha Bergman Watanabe & Burton LLP

(57) ABSTRACT

An apparatus to test a drilling fluid in a laboratory includes a test cell configured to test the fluid to determine a Sag Factor of the fluid. The test cell may be heated with a heating jacket to a predefined temperature. A plurality of densitometers are configured to continuously measure a density of the fluid circulating in the test cell. A computing device processes the density measurements to determine a Sag Factor of the drilling fluid.

10 Claims, 5 Drawing Sheets

(56) References Cited

U.S. PATENT DOCUMENTS

| | | | |
|---|---|---|---|
| 10,914,664 B1 | 2/2021 | Miller et al. | |
| 10,947,843 B2* | 3/2021 | Jamison | G01N 9/26 |
| 11,555,733 B2* | 1/2023 | Beckett | G01F 23/363 |
| 11,643,898 B2* | 5/2023 | Gao | E21B 31/03 |
| | | | 166/250.01 |
| 11,739,636 B2* | 8/2023 | Jamison | G01N 9/26 |
| | | | 73/152.55 |
| 11,781,054 B1* | 10/2023 | Elkatatny | C09K 8/145 |
| | | | 175/65 |
| 11,827,837 B2* | 11/2023 | Mohamed | C09K 8/14 |
| 11,840,926 B2* | 12/2023 | Everhard | G01N 9/26 |
| 2013/0312511 A1* | 11/2013 | Jamison | G01N 15/04 |
| | | | 73/152.05 |
| 2014/0291023 A1 | 10/2014 | Edbury et al. | |
| 2016/0208600 A1* | 7/2016 | Gisolf | E21B 49/081 |
| 2016/0238504 A1* | 8/2016 | Jamison | G01N 9/00 |
| 2017/0131429 A1* | 5/2017 | Schneider | G01V 5/101 |
| 2018/0171774 A1 | 6/2018 | Ringer et al. | |
| 2018/0266197 A1* | 9/2018 | Amanullah | G01N 15/082 |
| 2018/0275112 A1* | 9/2018 | Lee | B01J 19/0006 |
| 2020/0124513 A1* | 4/2020 | Gao | E21B 31/03 |
| 2020/0182852 A1* | 6/2020 | Stewart | G01N 9/36 |
| 2020/0317981 A1* | 10/2020 | Mohamed | C09K 8/16 |
| 2021/0054255 A1* | 2/2021 | Elkatatny | C09K 8/36 |
| 2021/0199486 A1* | 7/2021 | Beckett | G01N 9/18 |

OTHER PUBLICATIONS

Ofei et al. "Laboratory Evaluation of Static and Dynamic Sag in Oil-Based Drilling Fluids," SPE 199567 (Year: 2021).*

Kulkarni, Sandeep D. et al., "Modeling Real-Time Sag in the Wellbore", SPE-178832-MS, paper presented at the IADC/SPE Drilling Conference and Exhibition, Fort Worth, Texas, USA, Mar. 2016 (13 pages).

Zamora, Mario et al., "Innovative Devices for Testing Drilling Muds", SPE Drilling Engineering 5(1), pp. 11-16, Mar. 1990 (6 pages).

Zamora, Mario, "Mechanisms, Measurement And Mitigation Of Barite Sag", OMC-2009-105, paper presented at the Offshore Mediterranean Conference and Exhibition, Ravenna, Italy, Mar. 2009 (14 pages).

Murphy, Robert Jerome at al., "Apparatus for Measuring the Dynamic Solids Settling Rates in Drilling Fluids", SPE-103088-MS, paper presented at the SPE Annual Technical Conference and Exhibition, San Antonio, Texas, USA, Sep. 2006 (9 pages).

"Embedded Sensors;" Integrated Sensing Systems; Accessed May 20, 2024; Retrieved from the Internet: URL: https://metersolution.com/embedded-sensors/ (2 pages).

* cited by examiner

APPARATUS AND METHOD FOR MEASURING SETTLING OF WEIGHTING MATERIALS IN DRILLING AND COMPLETION FLUIDS

BACKGROUND

While drilling a gas or oil well, a drilling fluid, i.e. mud, is typically pumped down to the drill bit during drilling operations and flowed back to the surface through the annulus defined between the drill string and the walls of the borehole. A typical drilling fluid includes a weighting material, such as barite, to increase the density of the drilling fluid and thereby assist in transporting rock chips and cuttings from the drill bit to the surface. As the mud is circulated through the drill string and returned through the surrounding annulus, the drill bit may be cooled and the drilled cuttings may be circulated to the surface. However, in some instances, added solid particles and borehole cuttings may settle out from the mud either at the bottom of the borehole or on the bottom-side of an inclined wellbore. This is a known and persistent problem in drilling operations and is known as "sag" or "barite sag" and may lead to unstable fluid rheological behavior. Turbulence in the moving fluid may tend to keep particles in suspension, but when the drilling fluid becomes static, such as while tripping the drill bit or when the circulation flow rate of the drilling fluid is relatively low, the weighting material(s) may tend to settle toward the bottom of the borehole. If solid particles settle downward, the drilling mud becomes density stratified. The created pressure imbalance may further accelerate the separation process and may lead to stuck drilling pipe, loss of circulation, and/or misdirection of the drilling path, any or all of which may be referred to as a "sag event."

Conventionally, one way to detect the occurrence of a mud sag is by comparing the mud-out weight (i.e., as the mud leaves the wellbore) and the mud-in weight (i.e., as the mud enters the wellbore) measurements. However, the long time-delay between these two measurements significantly affects the method's accuracy and may lead to delay in activating sag mitigation procedures. Furthermore, uncertainties associated with the sensors can also lead to inaccurate predictions (or uncertainties) of the mud's sag tendency. Another conventional method is to monitor the standpipe pressure as fluctuations in the pressure may indicate non-uniform flow resistance within the borehole. These methods are indirect, at best, and the variations in mud density and pressure may be caused by factors unrelated to sag.

A method to accurately predict real-time sag has been a long-standing need in the field. Despite multiple studies having been conducted to understand the sag phenomenon and to enhance drilling and completion fluids properties to minimize its occurrence, there remains few practical and accurate methodologies to quantify the settling rate and its severity so that more effective preventive measures can be taken and/or decisions made for fluids selection or interventions conducted.

A practical and accurate method for measuring settling of weighting materials contained in drilling and completion fluids could serve as a useful tool for mud engineers to evaluate and predict sag behavior. It could also enable fast decision making at the well to optimize fluid formulations and operating conditions for sag management.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to measurement of sag properties of drilling and completion fluids prior to use in a well. In another aspect, embodiments relate to prediction of sag in actual use conditions in a well. In yet another aspect, embodiments relate to methods for performing the aforementioned measurements and predictions, and systems for accomplishing or performing such measurements and predictions.

In one aspect, embodiments disclosed herein relate to an apparatus to test a fluid in a laboratory. The apparatus includes a test cell configured to test the fluid to determine a Sag Factor of the fluid, a heating jacket configured to receive the test cell and heat the test cell to a predefined temperature, a plurality of densitometers configured to continuously measure a density of the fluid circulating in the test cell, and at least one data line for transmitting the density measurements from the test cell to a computing device in the laboratory, wherein the computing device is configured to process the density measurements to determine a Sag Factor of the drilling fluid.

In one aspect, embodiments disclosed herein relate to a method for determining Sag Factor of a fluid. The method involves obtaining a sample of fluid to be analyzed, filling a laboratory test cell with the fluid to be analyzed, closing the laboratory test cell to seal the fluid inside and applying a selected pressure to the test cell, heating the laboratory test cell to a selected temperature, measuring a density of the fluid inside the laboratory test cell under the selected pressure and temperature, transmitting the density measurement to a computing device for processing; and determining a Sag Factor of the fluid in the laboratory test cell.

Other aspects and advantages of the claimed subject matter will be apparent from the following description and the appended claims.

BRIEF DESCRIPTION OF DRAWINGS

The following figures are included to illustrate certain aspects of the embodiments, and should not be viewed as exclusive embodiments. The subject matter disclosed is amenable to considerable modifications, alterations, combinations, and equivalents in form and function, as will occur to those skilled in the art and having the benefit of this disclosure.

DETAILED DESCRIPTION

Figure 1:
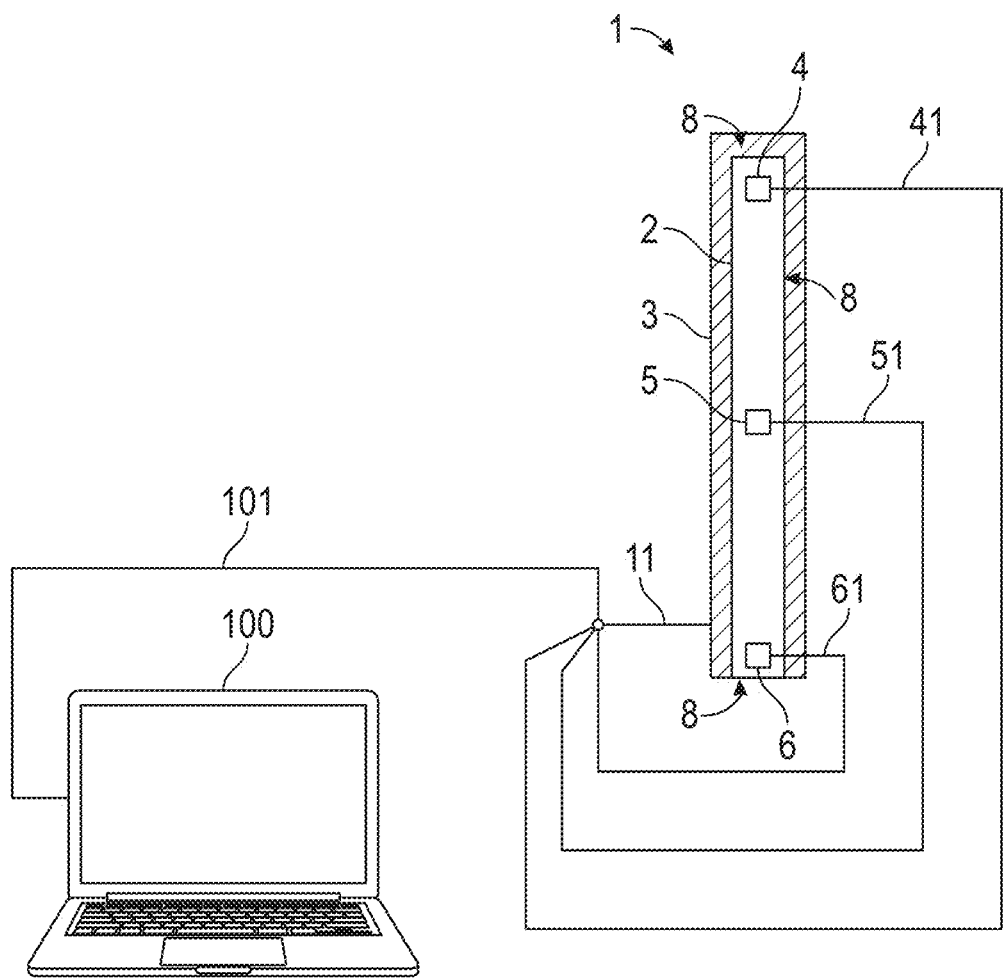
FIG. 1 is an illustration of an embodiment of a sag measurement system incorporating aspects of the disclosure.
Figure 2:
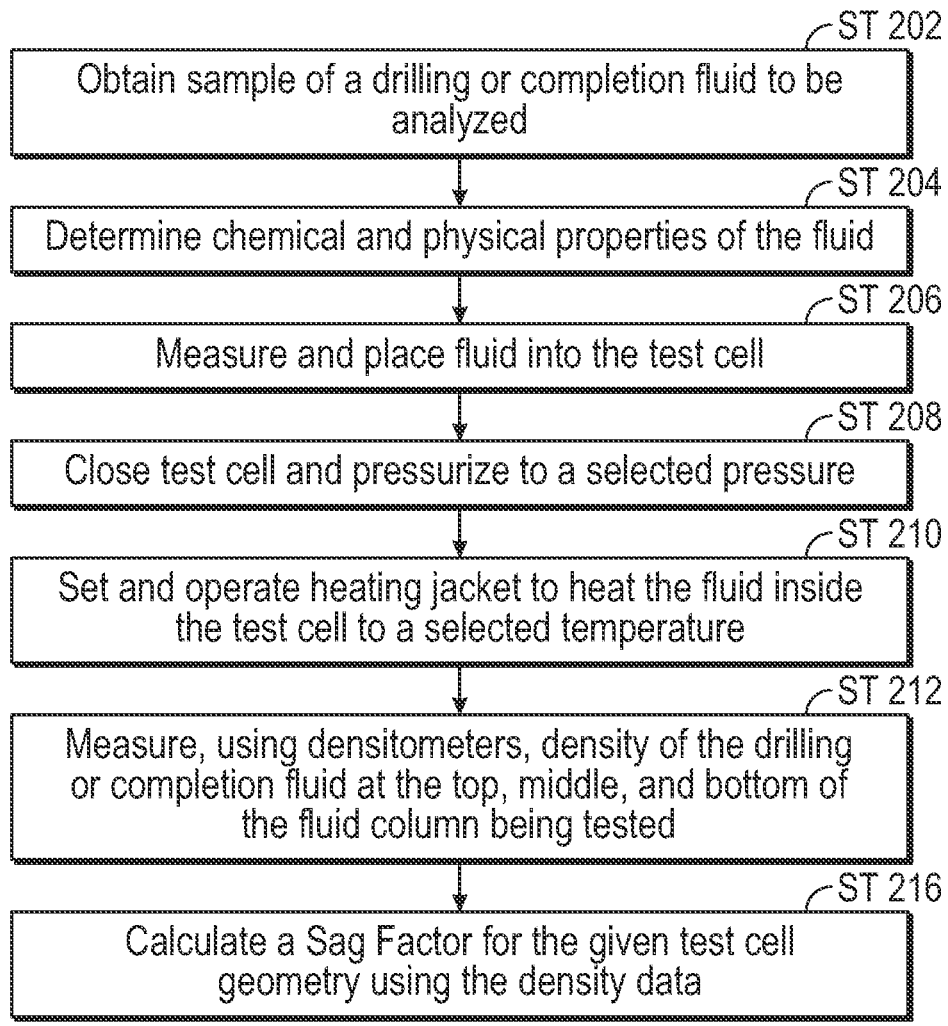
FIG. 2 is a flowchart of method steps for determining a Sag Factor of drilling fluid in a laboratory according to an embodiment of the disclosure.

Disclosed herein are methods and systems for characterizing real-time mud sag, and uses for the information and characterization thus obtained, thus enhancing workflow performance in the oil and gas exploration and production industry. More specifically, the present embodiments relate to a mud sag analyzing system for evaluation and characterization of Sag Factor of a circulating mud. The system includes both physics-based sag prediction models and data-driven sag detection aspects that allow for calculating Sag Factor based on settling rates. The quantitative Sag Factor may provide a framework for mitigation of mud sag using automatic control techniques.

In one aspect, embodiments disclosed herein relate to measurement of sag properties of drilling and completion fluids prior to use in a well. Sag is initiated by particle settling in the fluid. Particle sedimentation in Newtonian and non-Newtonian fluids has been the subject of much research. For a low Reynolds number flow regime (Re<<1), the drag force ($F_d$) on a spherical particle in a Newtonian fluid is described by:

$$F_d = 6\pi\eta\alpha\, U \quad \text{(Eq. 1)},$$

where $\alpha$ is particle radius, $\eta$ is fluid viscosity, and $U$ is rate of sedimentation. However, for sedimentation of particles in non-Newtonian fluids, Equation 1 must be modified to account for the fluid rheological properties, such as shear thinning/thickening, thixotropy, and viscoelasticity. Researchers in the field have reported that the viscometer sag shoe tester (VST) can potentially be used to predict barite sag from calculations as stated in Zamora, M., 2009, Mechanisms, measurements and mitigation of barite sag; presented at the Offshore Mediterranean Conference and Exhibition, Ravenna, Italy, 25-27 Mar. 2009; OMC-2009-105. Known wellbore sag modeling includes both rheological methods to estimate settling rates by mathematical solutions and experimental methods to estimate the particulate settling rate including running static aging tests at specified temperatures and pressures. Obtaining dynamic settling rates by testing fluids on the dynamic high-angle settling test (DHAST) instrument at specified conditions of temperature, pressure, and shear rate is described in Murphy, R. J., Jamison, D. E., Hemphill, T. et al., 2006, Apparatus for Measuring the Dynamic Solids Settling Rates in Drilling Fluids, presented at the SPE ATCE, San Antonio, Texas, USA, 24-27 Sep. 2006 SPE-103088-MS (http://dx.coi.org/10.2118/110404-MS). According to an embodiment of the disclosure, the use of densitometers to collect data for automated calculation of Sag Factor reduces time and human error involved in such currently known techniques.

Other models of drilling fluid sag are also known. However, the known methods for modeling sag behavior rely upon or include manual calculations, measurement errors due to human factors, and prolonged delays between obtaining samples and completing Sag Factor calculations, resulting in longer times required to replace or recondition the drilling fluid. Such delays may result in well control and stuck-pipe non-productive time incidents.

FIG. 1 illustrates an exemplary sag measurement apparatus 1 suitable for implementing the methods described herein. As illustrated, the apparatus 1 may include a test cell 2 for receiving a sample of a drilling fluid to be characterized. The test cell 2 may be constructed of stainless steel with a maximum operating temperature of 500° F. and pressure of 1,800 pounds per square inch (psi). The cell 2 according to this embodiment is cylindrical, has an internal volume of 175 ml with 9.3 cm internal length and internal diameter of 7.1 cm. Further, the test cell 2, being cylindrical, comprises at least two faces 8: two flat, round faces 8 disposed parallel to each other on opposite ends of the test cell 2, and a continuous, curved face 8 that extends between the two flat, round faces 8. In order to simulate environmental conditions typically encountered or expected to be encountered by drilling and completion fluids, the test cell is preferably a pressure vessel capable of maintaining the sample fluid at the just-mentioned maximum temperature and pressure. The internal volume of the test cell 2 may be pressurized by any known commercially available pressure-generating equipment (not shown), suitably connected in fluid communication with the internal volume of the test cell 2. As will be understood, the test cell 2 is equipped with appropriate ports and/or fluid conduit (not shown) for filling and emptying the test cell 2. According to the embodiment of FIG. 1, the test cell 2 is arranged to hold a generally vertical column of drilling or completion fluid to be characterized. In one or more embodiments, the test cell 2 is temperature adaptable.

Insofar as drilling fluids are typically used under conditions of elevated temperatures as well as pressures, test cell 2 as illustrated in the embodiment of FIG. 1 is enclosed within a heating jacket 3. The test cell 2 is configured to be placed or disposed within the heating jacket 3 such that the heating jacket 3 envelops or surrounds the test cell 2, where the heating jacket 3 covers at least two faces 8 of an exterior of the test cell 2 (i.e., a flat face 8 and a curved face 8). The heating jacket 3 is configured to simulate wellbore temperature conditions in a laboratory environment. To this end, heating jacket 3 is equipped with heating elements (not shown) and thermostatic temperature control devices (not shown) in any conventional manner as is known to persons having ordinary skill in the art. Conventional temperature and pressure sensors (not shown) are provided to sense environmental conditions within the test cell 2 and to provide corresponding temperature and pressure data via data line 11 and data bus 101 to a suitably programmed computer 100. Computer 100 may be any suitable computing device including commercially available desktop and laptop computers loaded with and running appropriate software. The computing device may also include a tablet, a thin computer, a smartphone, a gaming console, or any other suitable device with a processor and memory for executing the appropriate software. The computer 100 may be a computing device as shown in FIG. 5. Computing methods performed by computer 100 are described hereinbelow.

In the embodiment of FIG. 1, the test cell 2 is equipped with three densitometers, namely a top densitometer 4, a middle densitometer 5, and a bottom densitometer 6. As shown, the three densitometers 4,5,6 are arranged vertically in the test cell 2. Suitable densitometers for use in the illustrated embodiment include any suitable commercially available densitometers known to those of ordinary skill in the art, such as those manufactured by Mettler-Toledo, for example.

In one or more embodiments, the densitometers are configured to continuously monitor the density of the fluid in the test cell. Further, the densitometers 4, 5, 6 are configured to transmit, via one or more data lines, the density measurements to the computer operatively connected to the test cell.

Data line 41 associated with top densitometer 4 is in data communication with data bus 101 for providing density data at the top of the column of fluid being characterized to the computer 100. Data line 51 associated with middle densitometer 5 is likewise in data communication with data bus 101 for providing density data at the middle of the column of fluid being characterized to the computer 100. Data line 61 associated with bottom densitometer 6 is likewise in data communication with data bus 101 for providing density data at the bottom of the column of fluid being characterized to the computer 100. The particular data communication protocol selected for these and any other required or desired data communication pathways may be any conveniently commercially available scheme and forms no part of the disclosure.

The embodiment as just described in connection with FIG. 1 may be used in at least the following methods. In a first method, settling rate of a drilling or completion fluid may be determined at any desired temperature, pressure, and over any desired period of time of interest. By way of example only, the following testing method may be performed.

Initially, a sample of a drilling or completion fluid to be analyzed is obtained from a drilling fluid pit, tank, laboratory storage, or any other desired source (Step 202). Initial chemical and physical properties of the fluid may be determined including, initial density, pH, and rheological properties including yield point, low shear rheology (6/3 rpm), and gels strengths following API-13B recommended practices (Step 204). These three rheological measurements are fundamental for the particles' suspension properties in the drilling fluid. If those properties are low, the tendency of sagging or settling will be higher.

After the fluid to be characterized with respect to sag properties has been initially measured as described above, the fluid is placed into the test cell 2 (Step 206). For an embodiment of the test cell 2 having cylindrical shape, 9.3 cm internal length and 7.1 internal diameter, and internal volume of 175 ml, an amount of fluid is added so that a void space sufficient to allow for expansion of the fluid due to heating is provided. It is noted that for all practical purposes, the drilling or completion fluids with which the invention is used are substantially incompressible so that it is not necessary to take pressure into account when determining the appropriate void space. In the embodiment of the test cell 2 having the above-mentioned dimensions, the void space at the upper end of the cell should be about 1 cm for test temperatures up to about 300° F., about 1.5 cm for test temperatures from about 300° F. up to about 400° F., and about 2.5-3.0 cm for test temperatures from about 400° F. to about 500° F.

In accordance with the presently described embodiment, upon filling the test cell and leaving the void space as appropriate, the test cell 2 is closed and pressurized to any desired pressure, which may be 100 psi or any other pressure, including a pressure selected to simulate the conditions at a given depth in a given wellbore (Step 208). Also, the thermostatically-controlled heating jacket 3 is set and operated to heat the fluid inside the test cell 2 to any desired temperature, which may be a temperature also selected to simulate the temperature at a given position or depth in a given wellbore (Step 210). In one or more embodiments, the heating jacket is preheated to 10° F. (6° C.) above the desired test temperature. If necessary, the thermostat is adjusted during the procedure to maintain this temperature.

Once the testing apparatus according to the embodiment of FIG. 1 is completely set up, testing of sag characteristics may begin. The densitometers 4,5,6 provide data representative of density of the drilling or completion fluid at the top, middle, and bottom of the fluid column being tested (Step 212). In addition, temperature and pressure data may be obtained during the test period; temperature and pressure will usually be constant from the beginning to the end of the test period, but may be varied during the test as desired, as well. Data may be obtained continuously or sampled at specified or desired intervals. The test may be continued for any desired period of time, such as 48 hours, 72 hours, or any other duration.

The acquired density data may be used according to an aspect of an embodiment of the disclosure to calculate a parameter called Sag Factor for a given test cell geometry at any desired time after the start of the test (Step 216). Sag Factor is determined and calculated by the computer 100 using any conventional arithmetic calculating software as follows:

$$\text{Sag Factor}(t_n) = \text{SG Bottom}(t_n)/(\text{SG Bottom}(t_n) + \text{SG Top}(t_n)) \quad \text{(Eq. 3)}$$

where Sag Factor($t_n$) is Sag Factor at time n, SG Bottom($t_n$) is the calculated specific gravity of the fluid at the position of bottom densitometer 6 at time n, and SG Top($t_n$) is the calculated specific gravity of the fluid at the position of top densitometer 4 at time n, and wherein specific gravity of the fluid is calculated with the measured density.

Drilling fluids consist of several particles in suspension in a continuous phase that could be water or oil. Those particles in suspension have different specific gravity or density. One function of the drilling fluid is to suspend those particles and cuttings from the wellbore while drilling and, more importantly, in static conditions when not drilling. During the overall procedure of drilling a well, many activities involve d static conditions without circulation of drilling fluids through the well, such as tripping, wireline logging, blow-out preventer (BOP) testing, among many others. During those activities conducted in static conditions, the drilling fluid should provide the enough suspension capacity to prevent all or most of those solid particles falling down toward the bottom of the well, which can result in stuck pipe, loss of the hydrostatic drilling fluid pressure and, as a consequence, well control situations that will lead to non-productive time and increased cost of the well.

By calculating Sag Factor, the operator can proactively avoid those non-productive time incidents and save money to the well owner. Determining Sag Factor allows the operator to establish the appropriate drilling fluids suspension properties based on the provided well conditions. In case of unacceptably high Sag Factor, as will be further explained, drilling fluid particle suspension properties must be conditioned to reduce Sag Factor. The drilling fluids properties that primarily directly affect the suspension properties are yield point, low shear rheology (6/3 rpm), and gels strengths.

Sag Factor may be a useful indicator of acceptability of a given drilling mud design at a specified time and under particular temperature and pressure conditions. For example, for a drilling fluid or mud that is expected to be used for 72 hours and then replaced, in a wellbore environment having a temperature of 400° F. and a pressure of 100 psi, the embodiment as just described in connection with the apparatus illustrated in FIG. 1 may be used to perform a laboratory test of the sag characteristics of that fluid before it is deployed downhole. In this example, when the calculated Sag Factor is about 0.50 at the completed full time of the test designed to simulate actual wellbore conditions, it is anticipated that sag will not occur, and drilling and completion operations will not be adversely impacted by any sag event. If, however, the calculated Sag Factor is between about 0.50 and 0.53, some acceptable amount of sage may be expected to occur, but the drilling fluid design is still considered to be acceptable. If, however, the calculated Sag Factor is more than about 0.53, then sag will occur and may result in a sag event that produces undesirable consequences on drilling operations.

Sag Factor is time-dependent and does not depend on the height of the test cell. Drilling fluids consist of several particles in suspension in a continuous phase that could be water or oil. Those particles in suspension have different specific gravity or density. The suspension properties are achieved with viscosifiers and rheology modifier additives that are directly mixed into the drilling fluids. The performance of those suspension additives is affected by time, especially in static conditions, and also temperature and the pressure. When temperature and pressure increase the rates of degradation of the main components of the viscosifiers and rheology modifiers are affected, impacting negatively the suspension properties of the drilling fluid, resulting in a higher tendency to sagging. Similarly, the longer is the time of the fluids in the wellbore, the higher the sagging tendency will be as the suspension properties of the fluid are affected by temperature and pressure effects.

The following examples of Sag Factor determination were conducted in the above-described embodiment of the test cell 2.

Example 1

| MUD TYPE | | | | OBM | | |
|---|---|---|---|---|---|---|
| READING | | L600 | | 67 | | |
| READING | | L300 | | 44 | | |
| READING | | L200 | | 35 | | |
| READING | | L100 | | 25 | | |
| READING | | L6 | | 12 | | |
| READING | | L3 | | 13 | | |
| GEL STRENGHT 10 SEC | | Lb/100 ft2 | | 17 | | |
| GEL STRENGHT 10 MIN | | Lb/100 ft2 | | 31 | | |
| PLASTIC VISCOSITY | | CP | | 23 | | |
| YIELD POINT | | Lb/100 ft2 | | 21 | | |
| MUD WEIGHT | pcf | 81 | 81 | 81 | 81 | 81 | 81 |
| STATIC AGE | HRS | 12 | 24 | 36 | 48 | 60 | 72 |
| SAG FACTOR | | 0.51 | 0.525 | 0.527 | 0.529 | 0.531 | 0.535 |

In the foregoing and following data, the following terms have the meanings indicated:

OBM: Oil Base Mud

L600: 600 rpm reading from viscometer

CP: centipoise pcf: pounds per cubic foot

Example 2

| MUD TYPE | | | WBM | |
|---|---|---|---|---|
| READING | | L600 | 73 | |
| READING | | L300 | 54 | |
| READING | | L200 | 46 | |
| READING | | L100 | 35 | |
| READING | | L6 | 17 | |
| READING | | L3 | 19 | |
| GEL STRENGHT 10 SEC | | Lb/100 ft2 | 21 | |
| GEL STRENGHT 10 MIN | | Lb/100 ft2 | 42 | |
| PLASTIC VISCOSITY | | CP | 19 | |
| YIELD POINT | | Lb/100 ft2 | 35 | |
| MUD WEIGHT | pcf | | 122 | 122 |
| STATIC AGE | HRS | | 1 week | 2 week |
| SAG FACTOR | | | 0.52 | 0.53 |

Example 3

| MUD TYPE | | | | OBM | | |
|---|---|---|---|---|---|---|
| READING | | L600 | | 92 | | |
| READING | | L300 | | 53 | | |
| READING | | L200 | | 39 | | |
| READING | | L100 | | 25 | | |
| READING | | L6 | | 9 | | |
| READING | | L3 | | 8 | | |
| GEL STRENGHT 10 SEC | | Lb/100 ft2 | | 15 | | |
| GEL STRENGHT 10 MIN | | Lb/100 ft2 | | 22 | | |
| PLASTIC VISCOSITY | | CP | | 39 | | |
| YIELD POINT | | Lb/100 ft2 | | 14 | | |
| MUD WEIGHT | pcf | 108 | 108 | 108 | 108 |
| STATIC AGE | HRS | 24 | 48 | 72 | 96 |
| SAG FACTOR | | 0.508 | 0.509 | 0.513 | 0.516 |

Example 4

| MUD TYPE | | | | OBM | | |
|---|---|---|---|---|---|---|
| READING | | L600 | | 67 | | |
| READING | | L300 | | 39 | | |
| READING | | L200 | | 29 | | |
| READING | | L100 | | 18 | | |
| READING | | L6 | | 7 | | |
| READING | | L3 | | 6 | | |
| GEL STRENGHT 10 SEC | | Lb/100 ft2 | | 10 | | |
| GEL STRENGHT 10 MIN | | Lb/100 ft2 | | 16 | | |
| PLASTIC VISCOSITY | | CP | | 28 | | |
| YIELD POINT | | Lb/100 ft2 | | 11 | | |
| MUD WEIGHT | pcf | 82 | 82 | 82 | 82 |
| STATIC AGE | HRS | 24 | 48 | 72 | 96 |
| SAG FACTOR | | 0.507 | 0.508 | 0.508 | 0.512 |

Example 5

| MUD TYPE | | OBM | OBM | OBM |
|---|---|---|---|---|
| READING | L600 | 82 | 62 | 84 |
| READING | L300 | 50 | 39 | 58 |
| READING | L200 | 36 | 30 | 46 |
| READING | L100 | 23 | 20 | 31 |

-continued

| READING | L6 | 7 | 8 | 6 |
| READING | L3 | 6 | 7 | 5 |
| GEL STRENGTH 10 SEC | Lb/100 ft2 | 7 | 8 | 6 |
| GEL STRENGTH 10 MIN | Lb/100 ft2 | 10 | 14 | 8 |
| PLASTIC VISCOSITY | CP | 32 | 23 | 26 |
| YIELD POINT | Lb/100 ft2 | 18 | 16 | 32 |
| MUD WEIGHT | pcf | 96 | 92 | 74 |
| STATIC AGE | HRS | 48 | 48 | 48 |
| SAG FACTOR | | 0.514 | 0.508 | 0.512 |

Example 6

| MUD TYPE | | OBM |
|---|---|---|
| READING | L600 | 87 |
| READING | L300 | 53 |
| READING | L200 | 40 |
| READING | L100 | 27 |
| READING | L6 | 11 |
| READING | L3 | 10 |
| GEL STRENGTH 10 SEC | Lb/100 ft2 | 17 |
| GEL STRENGTH 10 MIN | Lb/100 ft2 | 32 |
| PLASTIC VISCOSITY | CP | 34 |
| YIELD POINT | Lb/100 ft2 | 19 |

| MUD WEIGHT | pcf | 90 | 90 | 90 | 90 |
| STATIC AGE | HRS | 24 | 48 | 72 | 96 |
| SAG FACTOR | | 0.509 | 0.512 | 0.517 | 0.52 |

Example 7

| MUD TYPE | | WBM |
|---|---|---|
| READING | L600 | 58 |
| READING | L300 | 40 |
| READING | L200 | 33 |
| READING | L100 | 25 |
| READING | L6 | 15 |
| READING | L3 | 14 |
| GEL STRENGTH 10 SEC | Lb/100 ft2 | 21 |
| GEL STRENGTH 10 MIN | Lb/100 ft2 | 56 |
| PLASTIC VISCOSITY | CP | 18 |
| YIELD POINT | Lb/100 ft2 | 22 |

| MUD WEIGHT | pcf | 118 | 118 | 118 |
| STATIC AGE | HRS | 1 week | 2 week | 17 days |
| SAG FACTOR | | 0.516 | 0.52 | 0.523 |

The computing device or computer, such as that shown in FIG. 4 and described in further detail below, data collection and processing, and calculations of the embodiments described herein may be performed using hardware and software to implement the various illustrative blocks, modules, elements, components, methods, and algorithms described herein, and can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable programmable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Data transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Sag Factor may be used to determine critical drilling fluid circulating time for fluid treatment, replacement, or customization, based on modification of a formula for calculation of Circulation Time, $C_{time}$, as follows:

$$C_{time} = ((\Sigma \text{Effective Length})/(\text{Section Length})) * \text{Bottoms Up},$$

where,

Effective Length=Section Length×Section Length Factor (based on hole diameter and well inclination, as explained in the chart below), X Effective Length is the sum of all Effective Lengths for a given well, measured in feet, Section Length is the distance to which a specific hole section was drilled, measured in feet, Bottoms Up is the time the fluid take to travel from the bit to surface, depending on pumping rate, and can be measure in minutes or hours.

Section Length Factor is determined according to the following Table 1 for different hole diameters and well inclinations:

TABLE 1

| Well Inclination Range | Section Length Factor | | | |
|---|---|---|---|---|
| | 17½ inch hole | 12¼ inch hole | 8½ inch hole | 6⅛ inch hole |
| 0°-10° | 1.5 | 1.3 | 1.3 | 1.2 |
| 10°-30° | 1.7 | 1.4 | 1.4 | 1.3 |
| 30°-60° | 2.5 | 1.8 | 1.6 | 1.5 |
| 60°+ | 3.0 | 2.0 | 1.7 | 1.6 |

Next, as previously described and now shown in the following Table 2, mud condition is based on calculated Sag Factor as follows:

TABLE 2

| Sag Factor | Output |
|---|---|
| 0.5 | No sagging |
| 0.5 ≤ Sag Factor ≤ 0.53 | Mud is ok |
| Sag Factor > 0.53 | Sag will occur |

According to an embodiment of the disclosure, Sag Factor affects Circulation Time, $C_{time}$, according to the following Table 3:

TABLE 3

| Sag Factor | Output | Critical circulation time for fluid treatment, replacement, or customization |
|---|---|---|
| 0.5 | No sagging | Critical $C_{time}$ = ((Σ Effective Length)/(Section Length)) * Bottoms Up |
| 0.5 ≤ Sag Factor ≤ 0.53 | Mud is ok | Critical $C_{time}$ = ((Σ Effective Length)/(Section Length)) * Bottoms Up |
| Sag Factor > 0.53 | Sag will occur | Critical $C_{time}$ = ((Σ Effective Length)/(Section Length)) * Bottoms Up * 1.2 |

Example 8 is as follows. A well has a first 5024 foot section having a 17½ inch hole at 20° inclination, a second 12¼ inch section drilled to 16732 feet at 65° inclination, and a third 8½ inch section drilled to the final well length of 18244 feet also at 65° inclination. The Effective Lengths of the first, second, and third well sections, respectively, are 8540.8 feet, 33584 feet, and 31014.8 feet. The X Effective Length is 73139.6 feet. Assume that Bottoms Up time is 60 minutes. For Sag Factor up to 0.53, the Critical $C_{time}$ is as follows:

$$C_{time} = (73139.6 \text{feet}/18244 \text{feet}) * 60 \text{ minutes} = 240 \text{ minutes}$$

For Sag Factor greater than 0.53, Critical $C_{time}$ is as follows:

$$C_{time} = (73139.6 \text{feet}/18244 \text{feet}) * 60 \text{ minutes} * 1.2 = 289 \text{ minutes}$$

When sagging occurs the critical time to treat the system is higher, because the density of the fluid tends to reduce after the sagging, therefore additional time is required to treat the system with weighting agents to restore the required fluid density. Similarly, if fluid replacement or customization is required due well conditions, higher time is required.

Figure 3:
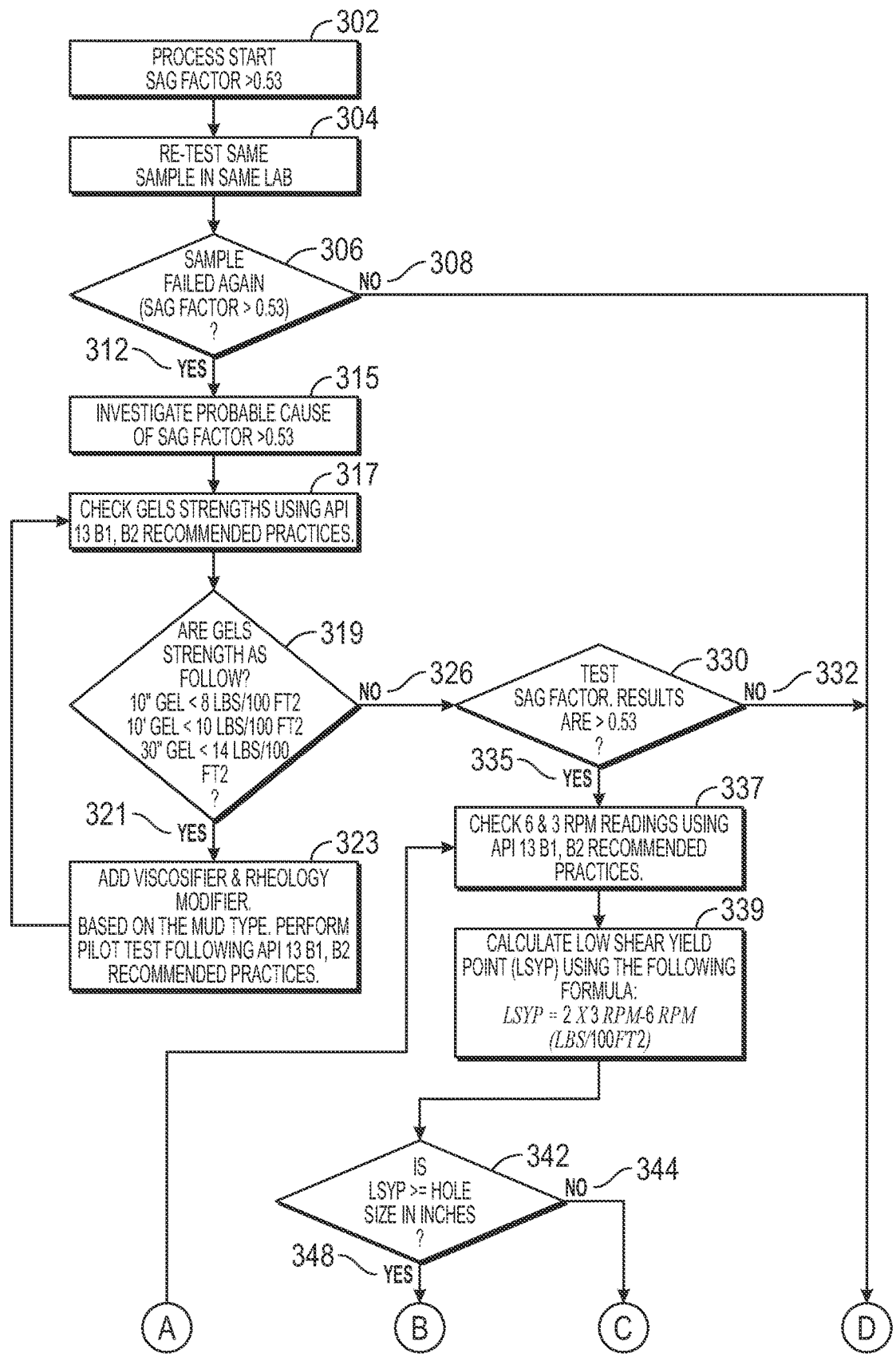
FIG. 3 is a flowchart for performing Sag Factor Root Cause Analysis and drilling fluid conditioning in accordance with an embodiment of the disclosure.
Figure 3:
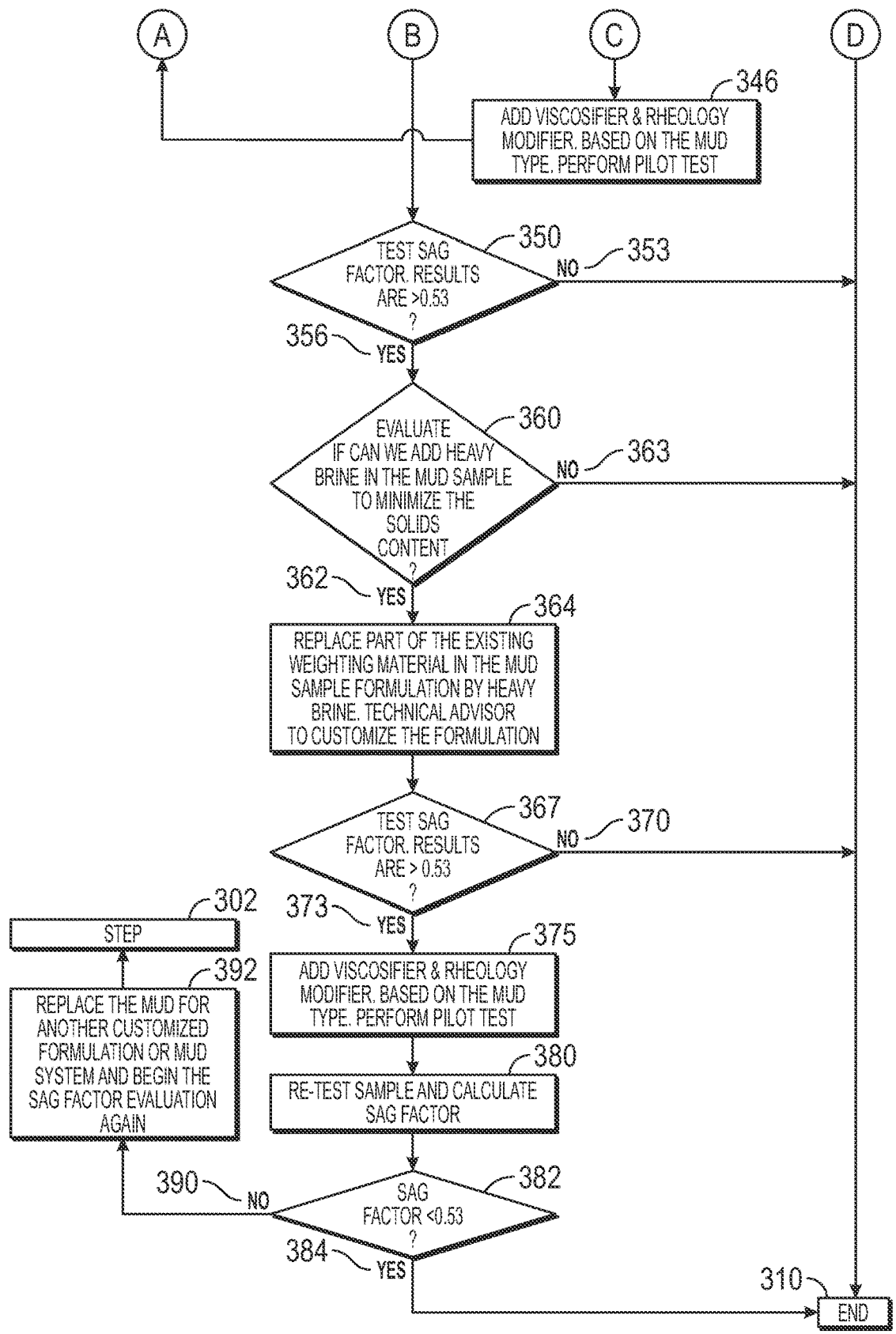

FIG. 3 illustrates in flow chart form a process for performing a Sag Factor Root Cause Analysis used to identify and, if desirable or necessary, correct various aspects of drilling fluids to modify the Sag Factor as determined in accordance with an embodiment. The process starts when Sag Factor is determined to be greater than 0.53 indicating that sag will occur (Step 302). The illustrated process should lead to an indication of the root cause and which steps to follow to condition the drilling fluid in order to enhance the rheological suspension properties of the fluid and then improve the Sag Factor to desired conditions (<0.53). The next step is to re-test the sample (Step 304) to verify the Sag Factor value in order to potentially avoid much time and unnecessary expense if the problem is with the original Sag Factor measurement. If Sag Factor is not greater than 0.53 (Steps 306, 308), the procedure is complete (Step 310).

If, on the other hand, Sag Factor is in fact greater than 0.53 (Steps 306, 312), investigation of the cause of the sagging failure begins (Step 315). A number of different variables need to be checked, the first being the gels strengths using API recommended practices 13B1 & 13B2, depending of the type of drilling fluid (Step 317). Gels strength are time-dependent measurements of a fluid's shear stress under static conditions and are commonly measured after 10-second, 10-minute, and 30-minute intervals. The detailed procedure how to calculate the gel strength is reflected in API Recommended Practices (RP) 13B-1 (for water-based mud) and API Recommended Practices 13B-2 (for oil-based mud) at section 7.3 for each RP. In case gel strengths are below the proposed range: 10" gel<8, 10' gel<10, 30' gel<14 (Steps 319, 321), viscosifiers and rheology modifiers need to be added to enhance the suspension properties of the fluid (Step 323). Depending on the type of drilling fluids, polymers, clays or fatty acids may need to be added. Once the correct additive to be added is identified, a pilot test needs to be performed to evaluate the proposed treatment and come up with the right concentration to be added. The pilot testing needs to be done once the right additive and concentration is identified, the additive need to be added at lab scale and mixed using a high-speed mixer for at least 15 minutes to produce a new conditioned sample. After completion of the pilot testing, the gels strengths are retested using API recommended practices 13B1 & 13B2 (Step 317), and this sub-process is repeated iteratively until the desitred gel strengths range is achieved.

Once gels strength are in desired range, Sag Factor is again determined (Steps 226, 330). If Sag Factor is less than 0.53, the root cause analysis process ends (Steps 332, 310). If Sag Factor is greater than 0.53, the next step is to study the important suspension property known as Low Shear Yield Point (LSYP). LSYP is often used as an indicator for sag potential and also as an indicator of the force required to get a drilling fluid to flow.

In order to calculate the LSYP, the 6 & 3 rpm readings from obtained with a rheometer using API recommended practices 13B1 & 13B2, depending on the type of drilling fluid Steps (335, 337). Once 6 & 3 rpm readings are known, the following formula is used to calculate LSYP:

$$\text{LSYP} = 2 \times 3 \text{ rpm} - 6 \text{ rpm (lbs per 100 sq.ft.) (Step 339)}$$

The LSYP should be equal to or greater than the hole size (in inches) where the drilling fluid is being used or is planned to be used (Step 342). In case the LSYP is lower than the hole size (in inches) where the drilling fluid is being used or is planned to be used, it will be necessary to add viscosifiers and rheology modifiers to enhance the suspension properties of the fluid (Steps 344, 346). Depending on the type of drilling fluids, polymers, clays, fatty acids may need to be added. Once the correct additive is identified, again a pilot test should be performed to evaluate the proposed treatment and a determination of the appropriate concentration to be added. The pilot testing needs to be done once the right additive and concentration is identified, the additive need to be added at lab scale, and then mixed using a high-speed mixer for at least 15 minutes, resulting in a new conditioned sample. After completing the pilot testing, LSYP is again measured using API recommended practices 13B1 & 13B2 and the above-mentioned formula (Steps 346, 337). If the value of LSYP is still out of range as per desired values, this sub-process is iteratively repeated until LSYP is in the desired range, at which time Sag Factor will again be determined (Steps 348, 350).

If Sag Factor is now below 0.53, the root cause analysis process ends (Steps 353, 310). If Sag Factor is still greater than 0.53 (Step 356), investigation of the weighting agent used in the formulation is called for.

One of the functions of the drilling fluid is to provide hydrostatic pressure to balance or over-balance the formation pressures and avoid well blow-out or loss-of-well-control situations. In order to increase or achieve the desired hydrostatic pressure, weighting additives are typically added to the fluid. Normally the specific gravity of those weighting additives ranges from 2.7 to 5 (and sometimes even higher). Those weighting additives are in suspension in the fluid and in static conditions tend to settle due to gravity. For this reason, the next step in the root cause analysis is to evaluate if any heavy brine (solids free) can be added in the fluid formulation to minimize the weighting additives concentration and solids in suspension content in the fluid (Step 360). If high density solids free brine can be used as weighting material, this option will provide higher density with reduced solids content, and therefore Sag Factor should be reduced. Based on the type of fluid and after a drilling fluids technical advisor reviews the conditions and determines that this option is feasible, then a pilot test needs to be performed following similar procedures as mentioned before, and then Sag Factor needs to be determined again (Steps 362, 364, 367). If this option is not feasible, it will be necessary to replace completely the drilling fluid for another customized formulation or fluid (Steps 363, 392), and the analytical process is started from the beginning (Step 302).

If Sag Factor is now less than 0.53, the root cause analysis process ends (Steps 370, 310). If, however, Sag Factor is still greater than 0.53, it will be desirable to add further viscosifiers and rheology modifiers in order to enhance the suspension properties of the fluid (Steps 373, 375). Depending on the type of drilling fluids, polymers, clays, fatty acids, may need to be added. Once the correct additive is identified, a pilot test should be performed to evaluate the proposed treatment and determine the correct concentration to be added. After such treatment, Sag Factor will again be determined (Step 380). If Sag Factor is less than 0.53, the root cause analysis process ends (Steps 382, 384). If, however, Sag Factor is still greater than 0.53, it will be necessary to replace completely the drilling fluid for another customized formulation or fluid (Steps 390, 392), and the analytical process is started from the beginning (Step 302).

As disclosed herein, embodiments of the present disclosure may provide at least one of the following advantages. Rather than only determine a tendency for sagging, embodiments disclosed herein provide actual values for sag rate associated with mud fluid that is static or being circulated in the annulus of a wellbore. Embodiments disclosed herein may be used to calculate mud rate for vertical or deviated wells/applications. Further, actual expected density profile and time critical values are provided by the software which receives the fluid density measurements from the densitometers in the test cell. Further, embodiments disclosed herein may be performed in a laboratory environment, which is much more cost effective than performing these calculations in a physical wellbore during drilling operations. Thus, a laboratory method (apparatus) for weighting materials settling detection is provided that is to be used during the well pre-planning phase which is critical to establish a baseline for further work. Additionally, embodiments disclosed herein employ density sensors to effectively determine the settling rate of the weighting materials or any solids in the drilling or completion fluids.

Figure 4:
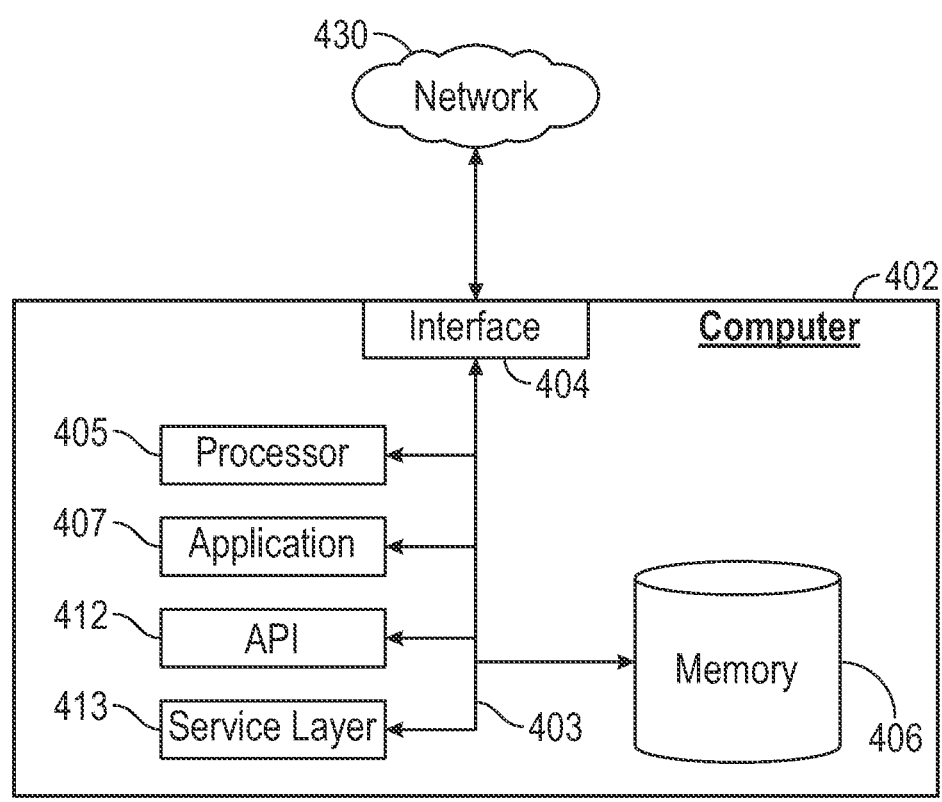
FIG. 4 shows a computing device in accordance with one or more embodiments.

Embodiments disclosed herein may be implemented on a computing device, such as the one shown in FIG. 4. FIG. 4 is a block diagram of a computer system (502) used to provide computational functionalities associated with described algorithms, methods, functions, processes, flows, and procedures as described in the instant disclosure, according to an implementation. The illustrated computer (502) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (502) may include a computer that includes an input device, such as a keypad, keyboard, touch screen, or other device that can accept user information, and an output device that conveys information associated with the operation of the computer (502), including digital data, visual, or audio information (or a combination of information), or a GUI.

The computer (502) can serve in a role as a client, network component, a server, a database or other persistency, or any other component (or a combination of roles) of a computer system for performing the subject matter described in the instant disclosure. The illustrated computer (502) is communicably coupled with a network (530). In some implementations, one or more components of the computer (502) may be configured to operate within environments, including cloud-computing-based, local, global, or other environment (or a combination of environments).

At a high level, the computer (502) is an electronic computing device operable to receive, transmit, process, store, or manage data and information associated with the described subject matter. According to some implementations, the computer (502) may also include or be communicably coupled with an application server, e-mail server, web server, caching server, streaming data server, business intelligence (BI) server, or other server (or a combination of servers).

The computer (502) can receive requests over network (530) from a client application (for example, executing on another computer (502)) and responding to the received requests by processing the said requests in an appropriate software application. In addition, requests may also be sent to the computer (502) from internal users (for example, from a command console or by other appropriate access method), external or third-parties, other automated applications, as well as any other appropriate entities, individuals, systems, or computers.

Each of the components of the computer (502) can communicate using a system bus (503). In some implementations, any or all of the components of the computer (502), both hardware or software (or a combination of hardware and software), may interface with each other or the interface (504) (or a combination of both) over the system bus (503) using an application programming interface (API) (512) or a service layer (513) (or a combination of the API (512) and service layer (513). The API (512) may include specifications for routines, data structures, and object classes. The API (512) may be either computer-language independent or dependent and refer to a complete interface, a single function, or even a set of APIs. The service layer (513) provides software services to the computer (502) or other components (whether or not illustrated) that are communicably coupled to the computer (502). The functionality of the computer (502) may be accessible for all service consumers using this service layer. Software services, such as those provided by the service layer (513), provide reusable, defined business functionalities through a defined interface. For example, the interface may be software written in JAVA, C++, or other suitable language providing data in extensible markup language (XML) format or other suitable format. While illustrated as an integrated component of the computer (502), alternative implementations may illustrate the API (512) or the service layer (513) as stand-alone components in relation to other components of the computer (502) or other components (whether or not illustrated) that are communicably coupled to the computer (502). Moreover, any or all parts of the API (512) or the service layer (513) may be implemented as child or sub-modules of another software module, enterprise application, or hardware module without departing from the scope of this disclosure.

The computer (502) includes an interface (504). Although illustrated as a single interface (504) in FIG. 4, two or more interfaces (504) may be used according to particular needs, desires, or particular implementations of the computer (502). The interface (504) is used by the computer (502) for communicating with other systems in a distributed environment that are connected to the network (530). Generally, the interface (504) includes logic encoded in software or hardware (or a combination of software and hardware) and operable to communicate with the network (530). More specifically, the interface (504) may include software supporting one or more communication protocols associated with communications such that the network (530) or interface's hardware is operable to communicate physical signals within and outside of the illustrated computer (502).

The computer (502) includes at least one computer processor (505). Although illustrated as a single computer processor (505) in FIG. 4, two or more processors may be used according to particular needs, desires, or particular implementations of the computer (502). Generally, the computer processor (505) executes instructions and manipulates data to perform the operations of the computer (502) and any algorithms, methods, functions, processes, flows, and procedures as described in the instant disclosure.

The computer (502) also includes a memory (506) that holds data for the computer (502) or other components (or a combination of both) that can be connected to the network (530). For example, memory (506) can be a database storing data consistent with this disclosure. Although illustrated as a single memory (506) in FIG. 4, two or more memories may be used according to particular needs, desires, or particular implementations of the computer (502) and the described functionality. While memory (506) is illustrated as an integral component of the computer (502), in alternative implementations, memory (506) can be external to the computer (502).

The application (507) is an algorithmic software engine providing functionality according to particular needs, desires, or particular implementations of the computer (502), particularly with respect to functionality described in this disclosure. For example, application (507) can serve as one or more components, modules, applications, etc. Further, although illustrated as a single application (507), the application (507) may be implemented as multiple applications (507) on the computer (502). In addition, although illustrated as integral to the computer (502), in alternative implementations, the application (507) can be external to the computer (502).

There may be any number of computers (502) associated with, or external to, a computer system containing computer (502), each computer (502) communicating over network (530). Further, the term "client," "user," and other appropriate terminology may be used interchangeably as appropriate without departing from the scope of this disclosure. Moreover, this disclosure contemplates that many users may use one computer (502), or that one user may use multiple computers (502).

In some embodiments, the computer (502) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (SaaS), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

In addition, the term "or" should be interpreted in an inclusive sense. Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps.

The particular embodiments disclosed herein are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. Embodiments of the invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

In the following claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. An apparatus to test a fluid in a laboratory, comprising:
   a test cell configured to test the fluid to determine a Sag Factor of the fluid;
   a heating jacket configured to receive the test cell and heat the test cell to a predefined temperature;
   a plurality of densitometers configured to continuously measure a density of the fluid disposed in the test cell; and
   at least one data line for transmitting the density measurements from the test cell to a computing device in the laboratory,
   wherein the computing device is configured to process the density measurements to determine the Sag Factor of the fluid, and
   wherein the heating jacket covers at least two faces of an exterior of the test cell.

2. The apparatus of claim 1, wherein the plurality of densitometers comprises a first densitometer disposed on a bottom of the test cell, a second densitometer disposed in a middle of the test cell, and a third densitometer disposed on a top of the test cell.

3. The apparatus of claim 1, wherein the fluid is drilling fluid or completion fluid.

4. The apparatus of claim 1, wherein the heating jacket is preheated to 10° F. above the desired test temperature.

5. The apparatus of claim 1, wherein the test cell comprises a closure that seals the fluid in the test cell.

6. A method for determining a Sag Factor of a fluid, comprising:
   obtaining a sample of the fluid to be analyzed;
   filling a laboratory test cell with the fluid to be analyzed;
   closing the laboratory test cell to seal the fluid inside and applying a selected pressure to the laboratory test cell;
   heating, via a heating jacket that covers at least two faces of an exterior of the laboratory test cell, the laboratory test cell to a selected temperature;
   measuring, via a plurality of densitometers, a density of the fluid inside the laboratory test cell under the selected pressure and temperature;
   transmitting the density measurement to a computing device for processing; and
   determining the Sag Factor of the fluid in the laboratory test cell.

7. The method of claim 6, further comprising: determining initial properties of the fluid to be analyzed, wherein the initial properties comprise initial density, pH, and rheological properties.

8. The method of claim 6, wherein the selected temperature and the selected pressure are selected to simulate conditions at a given depth in a wellbore.

9. The method of claim 6, further comprising: measuring, via the plurality of densitometers, the density of the fluid at a top, a middle, and a bottom of the laboratory test cell.

10. The method of claim 6, wherein filling the fluid in the laboratory test cell comprises leaving a void for expansion of the fluid, wherein a size of the void to leave in the laboratory test cell depends on the selected temperature.

* * * * *